United States Patent [19]

Wolanin et al.

[11] Patent Number: 4,771,038

[45] Date of Patent: Sep. 13, 1988

[54] HYDROXAMIC ACIDS

[75] Inventors: Donald J. Wolanin, Wilmington, Del.; Andrew Shaw, Kennett Square, Pa.

[73] Assignee: ICI Americas Inc., Wilmington, Del.

[21] Appl. No.: 2,814

[22] Filed: Jan. 13, 1987

[30] Foreign Application Priority Data

Jan. 21, 1986 [GB] United Kingdom ............... 8601638

[51] Int. Cl.$^4$ .................. A61K 37/02; C07K 5/08
[52] U.S. Cl. .................................... 514/18; 530/331
[58] Field of Search ........................... 514/18; 530/331

[56] References Cited

PUBLICATIONS

Proc. of the Soc. for Experimental Biol. and Med. 183, 262–267 (1986).

Primary Examiner—Delbert R. Phillips
Attorney, Agent, or Firm—Rosemary M. Miano

[57] ABSTRACT

This invention provides a series of novel hydroxamic acids of formula I which are useful as inhibitors of metalloproteases such as endopeptidases.

6 Claims, No Drawings

HYDROXAMIC ACIDS

BACKGROUND OF THE INVENTION

The present invention comprises certain hydroxamic acids as inhibitors of metalloproteases, methods for their preparation, pharmaceutical compositions containing them and intermediates used in their preparation.

Selected hydroxamic acids have been suggested as collagenase inhibitors as in U.S. Pat. No. 4,599,361 to Dickens et al. Other hydroxamic acids have been suggested as angiotensin converting enzyme (ACE) inhibitors as may be seen, for example, in U.S. Pat. Nos. 4,105,789 to Ondetti et al. and 4,154,937 to Cushman et al. Still other uses for hydroxamic acids have included the inhibition of enkephalinase as may be seen in U.S. Pat. No. 4,496,540 to Kim and EPO application No. 82402314.7 (Publication No. 0 082 088).

SUMMARY OF THE INVENTION

The compounds of this invention are selected peptide-containing hydroxamic acids which are useful as inhibitors of the activity of metalloproteases, and in particular, endopeptidases such as proteoglycan degrading enzymes and collagenase. Such inhibitory activity may be useful whenever it is desired to achieve such an effect and may also be useful in various diseases in which the activity of such enzymes has been implicated, e.g., osteoarthritis. See Woessner, et al., *J. Biological Chem.*, Vol. 259, No. 6, pages 3633–3638 (1984); and Phadke, *J. Rheumatol.*, Vol. 10, pages 852–860 (1983) for a discussion of the activity of these enzymes in osteoarthritis.

DETAILED DESCRIPTION OF THE INVENTION

The invention relates to hydroxamic acids of formula I:

(Formula set out on pages following Examples)    I wherein
$R^1$ is a hydrophobic group such as a straight or branched chain (2–7C)alkyl:
$R^2$ and $R^3$ are each an amino acid residue:
n is 1 or 2; and
A is hydrogen or a group of the formula IA:

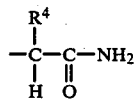
   IA wherein $R^4$ is an amino acid residue, and the pharmaceutically acceptable acid or base salts thereof, and other suitable derivatives, for example, maleate esters.

Particular values for the compounds of formula I include those in which
$R^1$ is selected from a group consisting of isobutyl and n-pentyl;
$R^2$ and $R^3$ are each independently selected and are each derived from a group of amino acid residues consisting of those derived from glycine, alanine, valine, leucine, isoleucine, phenylalanine, tyrosine, tryptophan, serine, threonine, cysteine, methionine, asparagine, glutamine, lysine, arginine, glutamic acid and aspartic acid. These residues do not have an acidic terminus, but may have an acidic side chain.

$R^4$ is selected from a group of particular values defined for $R^2$ and $R^3$;
n=1; and
A is as defined above.

More particular values for $R^2$ and $R^3$ include glycine, tyrosine, tryptophan, serine, threonine, cysteine, methionine, asparagine, glutamine, lysine, arginine, glutamic acid and aspartic acid.

Preferred values include those compounds in which
$R^1$ is isobutyl or n-pentyl;
$R_2$ is leucine or valine;
$R^3$ is alanine or phenylalanine;
n=1;
A is hydrogen.

Particularly preferred compounds are the following: (a) (R,S)-N-[2-[2-hydroxyamino)-2-oxoethyl]-1-oxoheptyl]-L-leucyl-L-phenylalaninamide (Example 1a); (b) (R,S)-N-[2-[2-(hydroxyamino)2-oxoethyl)-1-oxoheptyl]-L-leucyl-L-alaninamide (Example 3a); (c) N-[2-[2-(hydroxyamino-2-oxoethyl]-1-oxoheptyl]-L-valyl-L-alaninamide (Example 4a): and (d) (R,S)-N-[2-[2-(hydroxyamino)-2-oxoethyl]-4-methyl-1-oxopentyl1-L-leucyl-L-phenylalaninamide (Example 5a). It is also preferred that $R^2$ and $R^3$ be of the L configuration.

It will be appreciated by those skilled in the art that certain of the compounds of formula I contain three or more asymmetrically substituted carbon atoms, for example, chiral centers exist at the carbon atoms marked with an asterisk in formula I. Such compounds may exist in and be isolated in optically active and racemic forms. It has been found that the activity of the individual isomers is not the same, it is therefore preferred to utilize the more active isomer. It has also been found that mixtures of isomers, e.g., 50/50, exhibit activity and such active mixtures are also included within the scope of the invention. It will be further appreciated by those skilled in the art that optically active forms may be prepared by resolution of the racemic form or by synthesis from optically active starting materials and that active compounds and mixtures may be determined by tests hereinafter described.

The compounds of the invention may be made by hydrogenation of a compound of formula II:

(Formula set out on pages following Examples)    II

The compounds of formula II may be made by making a diacid of formula III:

(Formula set out on pages following Examples)    III such as by alkylating a trialkyl tricarboxylate of formula IIIa:

(Formula set out on pages following Examples)    IIIa where $R^5$ is methyl or ethyl, with subsequent hydrolysis and decarboxylation to give a compound of formula III. Alternatively, and more preferably, a Stobbe condensation may be performed with diethylsuccinate and an aldehyde of formula $R^6$CHO in strong base, where $R^6$ is straight or branched chain (1–6C)alkyl or phenyl, followed by hydrogenation and saponification to yield compounds of formula III.

The compound of formula III is then cyclized to obtain a compound of formula IV:

(Formula set out on pages following Examples)      IV

The ring is then opened with O-benzyl hydroxylamine to form an O-protected hydroxamic acid of formula V:

(Formula set out on pages following Examples)      V

The compound of formula V is then coupled with a dior tripeptide of formula VI:

(Formula set out on page following Examples)      VI (which, in turn, may be made by conventional peptide synthesis techniques) to give a compound of formula II.

The potency of compounds of the present invention to act as inhibitors of metalloproteases was determined by use of one or more of the following tests.

Chondrocyte Proteoglycanase Inhibition—For this test proteoglycan-degrading enzyme activity was measured by using the proteoglycan-polyacrylamide bead assay described by Nagase et al in *Anal. Biochem.*, 107: 385-392 (1980). The proteoglycan subunits were prepared as follows: Frozen bovine nasal septum used in the preparation of the subunits was obtained from Pel-Freez Biologicals, Rogers, Arizona. Guanidine hydrochloride (grade 1) was obtained from Sigma Chemical Co., St. Louis, Missouri. Celite ® acid-washed diatomite filter aid was supplied by Johns-Manville, Denver, Colorado. All other chemicals were of reagent or the best grade available.

The proteoglycan subunit was prepared from bovine nasal cartilage according to the procedure of Hascall et al, *J. Biol. Chem.*, 244: 2384-2396(1969), as modified by Roughly et al, *J. Biol. Chem.*, 255: 217-224(1981). Briefly, the cartilage was extracted with 4M guanidine hydrochloride containing 100 mM sodium acetate, 1 mM EDTA, 5 $\mu$g pepstatin/ml, 5 mM phenanthroline, and 0.02% sodium azide and adjusted to pH 6. The extraction mixture was stirred at 4° C. for 72 hr. The extraction mixture, with 5% diatomaceous earth (Hy-Flo Celite ®), was filtered through a coarse sintered-glass funnel. Cesium chloride was added to produce a specific gravity of 1.50. This extract was then centrifuged for 16 hr at 129,000×gravity and 8° C. in a DuPont OTD 65 ultracentrifuge according to the procedure of Radhakrishnamurthy et al. *Prep. Biochem.*, 10(2): 151-159 (1980). Gradient material with a specific gravity of 1.53 and greater, containing proteoglycan subunits, was retained and recentrifuged as above. Again, the gradient material with a specific gravity of 1.53 and greater was saved. The isolated proteoglycan subunits were dialized exhaustively against deionized water containing 0.02% sodium azide for 24 to 36 hr and then lyophilized.

The proteoglycan-polyacrylamide beads were prepared as described in Nagase et al., supra. The bead assay of enzyme activity was modified as follows. The assay solutions in the tubes contained 100 $\mu$l enzyme preparation and 100 $\mu$l buffer (Tris HCl, pH 7.4) or inhibitor in the buffer. Incubation with the beads was carried out at 37° C. for 6 or 20 hr. The degraded proteoglycan released from the polyacrylamide beads was determined assaying 100 $\mu$l spectrophotometrically at 535 nm with dimethylmethylene blue dye as described in Farndale et al, *Conn. Tissue Res.*, 9: 247-248 (1982). Chondroitin sulfate was used as a standard. One unit of proteoglycan-degrading activity is defined as the amount of enzyme required to release 1 $\mu$g chondroitin sulfate/ml-hr at 37° C.

Chondrocyte Collagenase Inhibition—Acid-soluble collagen was extracted from rat tail tendon by the method of Birkedal-Hansen et al, *Anal. Biochem.*, 115: 18-26 (1981) Rats were killed using $CO_2$ asphyxiation; tails were removed and stripped of skin. The tendons were removed and washed several times in cold distilled water. The salt-soluble collagen was removed by extracting the tendons twice (24 hr/extraction) in 1M NaCl, 50 mM Tris, and 5 mM $CaCl_2$, pH 7.4, at 4° C. The residue was washed twice in cold distilled water and extracted with 0.5M acetic acid for 24 hr. at 4° C. Insoluble material was removed by centrifugation (48,000×gravity for 1 hr), and NaCl (5% final concentration w/v) was added to the supernatant to precipitate the solubilized collagen. Following centrifugation (10,000×gravity for 30 min), the precipitate was redissolved in 0.5M acetic acid and dialyzed against 0.02M $Na_2HPO_4$. The precipitated type I collagen was centrifuged, redissolved in 0.5M acetic acid, and lyophilized. A portion of the collagen was $^{14}$C-acetylated using the method of Cawston et al, *Anal. Biochem.*, 99: 340-345 (1979) to give a specific activity of 1 $\mu$Ci/mg. Unlabeled and labeled collagen were mixed in a ratio of 4:1 (unlabeled: labeled) and solubilized in 5 mM acetic acid at 4° C. The collagen solution was brought to neutral pH and a final concentration of 2 mg/ml by the addition of an equal volume of 0.2M Tris base. One hundred microliters of neutralized collagen solution was dispensed into 500 -$\mu$l microfuge tubes and incubated at 35° C. overnight to allow fibril formation.

Enzyme samples were prepared as follows:

Chonodrocyte cultures. Cartilage slices were removed from the articular sufaces of 2-3 kg New Zealand white rabbits. Chondrocytes were liberated from the cartilage by sequential treatment with hyaluronidase, trypsin, and collagenase as described by Benya et al, *Biochem.*, 16: 865-872 (1977). The cells were seeded into culture flasks at a density of $3 \times 10^4$ cells/cm$^2$ in Ham's Nutrient Mixture F12 (Gibco, Grand Island, NY) supplemented with 10% fetal calf serum plus 25 $\mu$g/ml gentamicin and grown to confluency (7-10 days). The monolayers were changed to serum-free Dulbecco's Modified Eagle Medium (DMEM) with 25 $\mu$g/ml gentamicin plus 30-50 units/ml human interleukin-1 (IL-1), clarified Lipolysaccharide (LPS)-stimulated P388D$_1$ (obtained from American Type Culture Collection, Rockville, Md.) cell supernatant, or ammonium sulfate concentrated P388D$_1$ cell supernatant for 3 days. The stimulated chondrocyte supernatants were dialyzed against 50 mM Tris, 5 mM $CaCl_2$, 200 mM NaCl, 0.02% NaN$_3$ pH 7.4 (subsequently referred to as assay buffer) and stored at −20° C.

Enzyme samples to be assayed were dialyzed against an assay buffer consisting of 50 mM Tris, 200 mM NaCl, 5 mM $CaCl_2$, and 0.02% NaN$_3$, pH 7.4, at 35° C. Since collagenase is usally found in latent form, all samples were activated with 0.34 mM aminophenylmercuric acetate (APMA) for a minimum of 15 min at room temperature. Another dialysis was performed to remove APMA. A 100-$\mu$l aliquot of sample plus 100 $\mu$l assay buffer were added to the collagen fibrils and incubated for 18 to 24 hr at 35° C. The assays were terminated by centrifuging at 10,000×gravity for 10 min to precipitate the undigested collagen. The amount of solubilized collagen was determined by scintillation counting a 100-μl aliquot of the supernatant.

Compounds of the invention which were tested showed activity in one or both of these tests.

The following non-limiting examples are illustrative of the invention. Unless otherwise indicated:

(i) temperatures are in degrees Centigrade and procedures were carried out at room temperature, about 18°–26° C., unless otherwise indicated:

(ii) NMR spectra were determined at 250 MHz in DMSO-d$_6$ using tetramethylsilane (TMS) as an internal standard, and expressed as chemical shifts (delta values) in parts per million relative to TMS using the following abbreviations for designation of major peaks: s (singlet), m (multiplet), t (triplet). br (broad), d (doublet);

(iii) mass spectra data was obtained as described by the method explained in McLafferty, F. W., *Interpretation of Mass Spectra* (3rd ed. University Science Books, Mill Valley, California 1980) at pages 91–92.

(iv) where indicated the progress of reactions was monitored by thin layer chromatography (tlc);

(v) the following abbreviations have been used: g (gram), mg (milligram), l (liter), ml (milliliter), mmol (millimole), N (normal), M (molar), mM (millimolar), m.p. (melting point), min (minute), hr (hour), w (weight), v (volume), tlc (thin layer chromatography), R$_f$ (relative mobility in tlc), EtOAc (ethyl acetate), THF (tetrahydrofruan), MeOH (methyl alcohol), DMSO (dimethyl sulfoxide), Et$_2$O (diethyl ether), EDTA (ethylenediaminetetraacetic acid), Pd/C (palladium on charcoal catalyst), CI (continuous ionization), Ci (Curie).

In addition, chemical symbols have their usual meanings unless otherwise indicated. As a conversion factor 133.3 Pascals=1 Torr. Atmospheric pressue=104,308 Pascals. Conventional abbreviations for amino acids are also used (e.g., Leu (leucine), etc.).

EXAMPLE 1 a.
(R,S)-N-[2-[2-(Hydroxyamino)-2-oxoethyl]-1-oxoheptyl]-L-leucyl-L-phenylalaninamide (Formula I, R$^1$=n-pentyl, R$^2$=—CH$_2$CH(CH$_3$)$_2$, R$^3$=—CH$_2\phi$, A=H)

A portion of the material synthesized in Example 1e (0.52 g, 0.95 mmol) was dissolved in MeOH (60 ml), and 10% Pd/C (0.18 g) was added to the solution. The stirred mixture was subjected to hydrogen at atmospheric pressure until the starting material was absent by tlc. The catalyst was removed by passing the reaction mixture through a column of diatomaceous earth (Celite ®) and concentration of the filtrate gave the crude product as a solid. Recrystallization from hot MeOH/Et$_2$O gave 0.18 g (39% yield) of the title compound with a m.p. of 184°–186° C.

Analysis calculated for:
C$_{24}$H$_{38}$N$_4$O$_5$.0.6H$_2$O: C, 60.86; H, 8.34; N, 11.83, Found: C, 60.95; H, 8.21; N, 11.55, C, 60.85; H, 8.21; N, 11.52.

Pentylbutanedioic acid (Formula III, R$^1$=n-pentyl)

A method similar to that described by Devlin, et al, *J. Chem. Soc., Perkin Transactions I,* page 830 (1975) was used. Sodium ethoxide was formed by the addition of sodium metal (2.25 g, 91.59 mmol) to anhydrous EtOH (150 ml) under an N$_2$ atmosphere. To the resultant solution was added triethyl-1,1,2-ethanetricaboxylate (obtained from Aldrich; 21 ml, 91.59 mmol) followed by dropwise addition of n-pentyl bromide (11.4 ml, 91.59 mmol). The mixture was brought to reflux and stirred overnight (19 hr). After the reaction had cooled, it was filtered and concentrated. The residue was treated with H$_2$O and extracted with Et$_2$O (three times). The combined organic extracts were dried (MgSO$_4$), concentrated and purified by vacuum distillation (85° C./22.66 Pascals) to yield a colorless liquid (26.37 g, 91% yield).

Analysis calculated for:
C$_{16}$H$_{28}$O$_6$: C, 60.78; H, 8.86, Found: C, 60.80; H, 8.45, C, 60.82; H, 8.72.

All of the tricarboxylate was added to concentrated HCl (318 ml) and the resultant mixture was brought to reflux. Starting material was no longer visible by tlc after the reaction had proceeded for 44 hours. The reaction was extracted several times with a CHCl$_3$/THF (7:3) mixture. Product was removed from the combined organics by extracting with 2N NaOH. The aqueous extracts were acidified (concentrated HCl) to a pH of about 3 and were extracted with CHCl$_3$/THF (7:3), After the combined organic layers were dried (MgSO$_4$). removal of the solvent gave an off-white solid. Purification via gradient flash chromatography (SiO$_2$, 9:1 hexane/EtOAc to 10:1 CHCl$_3$/MeOH) gave 13.34 g (85%) of clean product: R$_f$=0.62 (SiO$_2$, 10:1 CHCl$_3$/MeOH).

Analysis calculated for:
C$_9$H$_{16}$O$_4$.0.05H$_2$O: C, 57.13; H, 9.05, Found: C, 57.19; H, 9.08, C, 57.29; H, 9.26.

c. Dihydro-3-pentyl-2,5-furandione (Formula IV, R$^1$=n-pentyl)

Most of the diacid synthesized in Example 1b (13.11 g, 69.69 mmol) was added to acetyl chloride (31.5 ml, 443 mmol) and the resultant mixture was brought to reflux. The starting material was consumed after 3 hours as evidenced by tlc. Removal of the volatile reaction components gave the desired product as a colorless liquid (12.40 g, 105% yield). Mass Spectrum (CI, isobutane): (M+1)=171. NMR (DMSO-d$_6$) 0.90 (3H;t, J=7), 1.29–1.40 (6H;m), 1.55–1.70 (1H;m), 1.80–2.00 (1H;m), 2.66 (1H;dt, J=10, 12.5), 3.00–3.14 (2H;m).

d. 2-[2-Oxo-2-(phenylmethoxyamino)ethyl]-heptanoic acid (Formula V, R$^1$=n-pentyl)

The O-benzylhydroxylamine for this experiment was produced via the following typical procedure: O-benzylhydroxylamine hydrochloride (100 mmol, obtained from Sigma) was dissolved in H$_2$O and treated with K$_2$CO$_3$(105 mmol). The aqueous mixture was extracted with Et$_2$O, dried (MgSO$_4$) and concentrated to provide near quantitative yields of the free base.

A dry round-bottom flask under an N$_2$ atmosphere was charged with a solution of the anhydride from Example 1c (12.40 g, 78.76 mmol) dissolved in dry THF (150 ml). The stirred solution was then cooled with a −20° C. bath. O-Benzylhydroxylamine (9.69 g, 78.76 mmol) was added slowly dropwise via syringe pump. After addition was completed, stirring was continued for 1 hr at −20° C. Volatiles were removed by rotary evaporation and the residue was taken up in EtOAc. The organic solution was washed with 10% HCl (three times), dried (MgSO$_4$) and concentrated to give a white solid. A non-polar impurity was removed by a gradient flash column (9:1 hexane/EtOAc to 24:1 CHCl$_3$/MeOH). Two recrystallizations from Et$_2$O/- hexane gave 6.85 g (32%) of the desired product; $R_f = 0.58$ (SiO$_2$, 20:1 CHCl$_3$/MeOH).

Analysis calculated for: C$_{15}$H$_{21}$NO$_4$C, 64.54; H, 7.52; N, 5.02, Found: C, 64.74; H, 7.56; N, 5.11, C, 64.76; H, 7.66; N, 5.16.

e.
(R,S)-N-[2-[2-Oxo-2-(phenylmethoxyamino)ethyl]-1-oxoheptyl]-L-leucyl-L-phenylalaninamide (Formula II R$_1$=n-pentyl, R$^2$=—CH$_2$CH(CH$_3$)$_2$, R$^3$=—CH$_2\phi$, A=H)

A portion of the material synthesized in Example 1d (1.05 g, 3.59 mmol) was dissolved in dry THF (50 ml) under N$_2$. The solution was treated with N-methyl morpholine (0.42 ml, 3.77 mmol) and the reaction mixture was then cooled with a bath at $-15°$ C. Ethylchloroformate (0.34 ml, 3.59 mmol) was added and the reaction was allowed to stir for 1 hr at $-15°$ C. A DMSO (15 ml) solution of LeuPheNH$_2$ (0.95 g. 3.43 mmol; synthesized via conventional peptide methodology) was then added dropwise. Once the addition was complete, the cooling bath was removed and the reaction was allowed to stir while warming to room temperature overnight. The mixture was diluted with Et$_2$O and washed successively with H$_2$O, 10% HCl (3 times), saturated NaHCO$_3$, and brine. Drying and concentration gave the crude product which was purified by flash chromatography (20:1 CHCl$_3$/MeOH) to provide 0.69 g (35% yield) of clean material having a m.p. of 194°-196° C.

Analysis calculated for: C$_{31}$H$_{44}$N$_4$O$_5$.0.4H$_2$O: C, 66.58; H, 8.06; N, 10.01, Found C, 66.60; H, 7.92; N, 9.92, C, 66.66; H, 7.95; N, 10.01,

EXAMPLE 2

Pentylbutanedioic acid (Formula III, R=n-pentyl)

An alternative method for synthesizing the compound of Example 1b is the following multistep procedure, the first part of which may be found in Johnson et al., *J. Amer. Chem. Soc.*, 67: 1357 (1945).

A 3-neck flask equipped with a condenser, addition funnel and an N$_2$ inlet was charged with potassium tert-butoxide (134.44 g, 1.10 mole; obtained from Aldrich) in dry tert-butanol (700 ml). After the solution was brought to reflux, dropwise addition of a mixture containing diethyl succinate (250 ml, 1.50 mole) and n-pentanal (106 ml, 1.00 mole) was begun. The reaction turned a deep orange. Reflux was continued for 1 hr. The reaction was cooled to room temperature and a solution of 200 ml concentrated HCl in 800 ml H$_2$O was added. The organic layer was separated and the aqueous layer discarded. Concentration of the organic layer gave the crude product mixture. This was diluted with EtOAc and extracted with saturated NaHCO$_3$ until acid product was absent from the organic layer. The aqueous extracts were acidified to a pH of about 3 with 10% HCl and extracted with Et$_2$O. The combined organic layers were dried (MgSO$_4$), rotary evaporated and vacuum distilled (101° C./33.3 Pascals) to yield unsaturated half-acid ester as a colorless oil (62.56 g, 30%). A solution of the unsaturated half-acid ester (62.14 g, 0.29 mole) in MeOH (500 ml) was added to a round-bottom flask containing 3.43 g of 10% Pd/C under N$_2$. The stirred mixture was then subjected to hydrogen at atmospheric pressure until uptake was no longer observed (about 13 hr). The catalyst was removed by filtration through diatomaceous earth (Celite ®) and the filtrate was concentrated by rotary evaporation. Vacuum distillation of the residue (100° C./58.65 Pascals) gave the saturated half-acid ester as a colorless oil (50.63 g, 81%). The saturated half-acid ester (50.63 g, 0.23 mole) was dissolved in EtOH (500 ml) and treated dropwise with 2N NaOH (586 ml). After standing at room temperature for 3 hr, the dark red reaction mixture was acidified to a pH of about 3 with 6N HCl and extracted with Et$_2$O. The combined organic extracts were washed first with H$_2$O, then with brine. Removal of volatiles followed by repeated concentration from hexane gave the crude product as a solid. Recrystallization from room temperature Et$_2$O/hexane gave 33.76 g (77% yield) of white solid which had the same properties as the compound of Example 1b.

EXAMPLE 3 a.
(R,S)-N-[2-[2-(Hydroxyamino)2-oxoethyl]-1-oxoheptyl]-L-leucyl-L-alaninamide (Formula I, R$^1$=n-pentyl, R$_2$=—CH$_2$CH(CH$_3$) hd 2, R$^3$=—CH$_3$ A=H)

Using the procedure described in Example 1a, hydrogenation of the compound synthesized in Example 3b gave 0.26 g (96% yield) of the title compound with a m.p. of 134°-136° C.

Analysis calculated for: C$_{18}$H$_{34}$N$_4$O$_5$.0.50H$_2$O: C, 54.66; H, 8.91; N, 14.17, Found: C, 54.95; H, 8.77; N, 13.59, C, 54.95; H, 8.82; N, 13.62.

b.
(R,S)-N-[2-[2-oxo-2-(phenylmethoxyamino)ethyl]-1-oxoheptyl]-L-leucyl-L-alaninamide (Formula II, R$^1$=n-pentyl, R$^2$=—CH$_2$CH(CH$_3$)$_2$, R$^3$=—CH$_3$, A=H)

Following the procedure outlined in Example 1e, a portion of the material synthesized in Example 1d (1.03 g, 3.50 mmol) was coupled with LeuAlaNH$_2$ (0.67 g, 3.34 mmol; LeuAlaNH$_2$ was synthesized via conventional peptide methodology). Workup followed by flash chromatography (15:1 CHCl$_3$/MeOH) gave 0.36 g (22% yield) of the title compound; Rf=0.26 (SiO$_2$, 15:1 CHCl$_3$/MeOH).

Analysis calculated for: C$_{25}$H$_{40}$N$_4$O$_5$: C, 63.04; H, 8.40; N, 11.76, Found: C, 63.18; H, 8.52; N, 11.10, C, 63.31; H, 8.47; N, 11.03.

EXAMPLE 4 a.
N-[2-[2-(Hydroxyamino-2-oxoethyl]-1-oxoheptyl]-L-valyl-L-alaninamide (Formula I, R$^1$=n-pentyl, R$^2$=—CH(CH$_3$)$_2$, R$^3$=—CH$_3$, A=H)

Using the procedure described in Example 1a, hydrogenation of the compound produced in Example 4b gave 0.35 g (0.77 mmol) of the title compound with a m.p. of 218°-220° C.

Analysis calculated for: C$_{17}$H$_{32}$N$_4$O$_5$: C, 53.93; H, 8.70; N, 14.79, Found: C, 54.04; H, 8.59; N, 14.49, C, 53.89; H, 8.56; N, 14.34.

b.
N-[2-[2-oxo-2-(phenylmethoxyamino)ethyl]-1-oxoheptyl]-L-valyl-L-alaninamide (Formula II, R$^1$=pentyl, R$^2$=—CH(CH$_3$)$_2$. R$_3$=—CH$_3$, A=H)

Using the procedure described in Example 1e, a portion of the material synthesized in Example 1d (0.96 g, 3.27 mmol) was coupled with ValAlaNH$_2$ (0.58 g, 3.13 mmol; ValAlaNH$_2$ was synthesized via conventional peptide methodology). Workup followed by flash chromatography (14:1 CHCl$_3$/MeOH) gave 0.42 g (27% yield) of the title compound, R$_f$=0.34 (SiO$_2$, 14:1 CHCl$_3$/MeOH).

Analysis calculated for: C$_{24}$H$_{38}$N$_4$O$_5$: C, 62.36; H, 8.22; N, 12.11, Found: C, 62.32; H, 7.97; N, 12.03, C, 62.23; H, 8.17; N, 11.97.

EXAMPLE 5 a.
(R,S)-N-2-[2-(hydroxyamino)-2-oxoethyl]-4-methyl-1-oxopentyl]-L-leucyl-L-phenylalaninamide (Formula I, R$^1$=—CH$_2$CH(CH$_3$)$_2$, R$^2$=—CH$_2$CH(CH$_3$)$_2$, R$^3$=—CH$_2\phi$, A=H Using the procedure of Example 1a, hydrogenation of the compound from Example 5e (0.53 g, 0.99 mmol) with subsequent recrystallization from hot MeOH/Et$_2$O gave 0.24 g (54% yield) of the title compound with a m.p. of 193°-195° C.

Analysis calculated for: C $_{23}$H$_{36}$N$_4$O$_5$.0.06H$_2$O: C, 60.20; H, 8.15; N, 12.21, Found: C, 60.05; H, 7.73; N, 11.97, C, 60.44; H, 7.99; N, 12.08 b. 2-(2-Methylpropyl)butanedioic acid (Formula III, R$^1$=—CH$_2$CH(CH$_3$)$_2$)

The procedures used in this example were the same as those described in Example 1b, except isobutyl bromide was used instead of n-pentyl bromide in the alkylation step. Thus, 22.6 g (91.6 mmol) of triethyl-1,1,2-ethanetricarboxylate were alkylated with 12.6 g (91.6 mmol) of isobutyl bromide. Subsequent distillation at 80° C. and 26.66 Pascals gave 23.7 g (86% yield) of an intermediate alkylated tricarboxylate.

Analysis calculated for: C$_{15}$H$_{26}$O$_6$.0.4H$_2$O: C, 58.09; H, 8.72, Found: C, 58.30; H, 8.22, C, 58.00; H, 8.37. Hydrolysis of the tricarboxylate by refluxing it with concentrated HCl gave 10.1 g (74% yield) of purified title compound; R$_f$=0.38 (SiO$_2$, 9:1 hexane/EtOAc).

Analysis calculated for: C$_8$H$_{14}$O$_4$: C, 55.19; H, 8.04, Found: C, 55.03; H, 8.45, C, 55.27; H, 8.49.

c. Dihydro-3-(2-methylpropyl)-2,5-furandione (Formula IV, R$^1$=—CH$_2$CH(CH$_3$)$_2$)

A major portion of the diacid synthesized in Example 5b (9.92 g, 57.00 mmol) was added to acetyl chloride (26 ml, 362.5 mmol) and the resultant mixture was brought to reflux. After 3 hr, the reaction was allowed to cool and the volatiles were removed to give the desired product as a colorless liquid (8.74 g, 98% yield); R$_f$=0.63 (7:3 hexane/EtOAc). Mass spectrum (CI, isobutane)-(M+1)=157. NMR (DMSO-d$_6$): 0.85 (3H; d, J=6), 0.89 (3H; d, J=6), 1.53-1.65 (3H; m), 2.73 (1H; dd, J=6.8, 18), 3.05 (1H; dd, J=9, 18), 3.20-3.40 (1H; m).

d.
4-Methyl-2-[2-oxo-2-(phenylmethoxyamino)ethyl]-2-pentanoic acid (Formula V, R$^1$=—CH$_2$—CH(CH$_3$)$_2$)

The anhydride (8.66 g, 55.47 mmol) formed in Example 5c was reacted with O-benzylhydroxylamine (6.83 g, 55.47 mmol) using the procedure described in Example 1d. A non-polar impurity was removed by gradient flash chromatography (9:1 hexane/EtOAc to 24:1 CHCl$_3$/MeOH). Recrystallization of the resultant off-white solid using Et$_2$O/hexane gave 6.30 g (41% yield) of a white solid; R$_f$=0.43 (SiO$_2$, 24:1 CHCl$_3$/MeOH). Mass spectrum (CI, isobutane) - (M+1)=280.

Analysis calculated for C$_{15}$H$_{21}$NO$_4$: C, 64.54; H, 7.52; N, 5.02, Found: C, 64.43; H, 7.29; N, 5.09, C, 64.74; H, 7.46; N, 5.12.

e.
N-[4-Methyl-2-[2-oxo-2-(phenylmethoxyamino)ethyl]-1-oxopentyl]-L-leucyl-L-phenylalaninamide (Formula II, R$^1$=—CH$_2$CH(CH$_3$)$_2$, R$^2$=—CH$_2$CH(CH$_3$)$_2$, R$^3$—CH$_2\phi$, A=H)

Using the procedure described in Example 1e, a portion of the material synthesized in Example 5d (1.25 g, 4.49 mmol) was coupled with LeuPheNH$_2$ (1.19 g, 4.28 mmol; LeuPheNH was synthesized via conventional peptide methodology). Workup followed by flash chromatography (14:1 CHCl$_3$/MeOH) gave material that was recrystallized from MeOH/H$_2$O to yield 0.53 g (22% yield) of the title compound with a m.p. of 208°-210° C.

Analysis calculated for: C $_{30}$H$_{42}$N$_4$O$_5$.0.3O: C, 66.27; H, 7.89; N, 10.30, Found: C, 66.30; H, 7.88; N, 10.29, C, 66.32; H, 7.86; N, 10.43.

EXAMPLE 6 a. 2-(2-Methylpropyl)butanedioic acid (Formula III, R$^1$=—CH$_2$CH(CH$_3$)$_2$)

An alternative method of making the title compound previously made in Example 5b is as follows. A procedure analogous to that described in Example 2 was followed using isobutyraldehyde instead of n-pentanal. Isobutyraldehyde (45 ml, 0.5 mole) was condensed with diethyl succinate (125 ml, 0.75 mole) employing potassium t-butoxide (67.22 g, 0.55 mole) as base in tert-butanol (500 ml) solution. After distillation at 105°-107° C. and 133.3 Pascals, workup gave 81.71 g of an intermediate unsaturated half-acid ester.

Analysis calculated for: C$_{10}$H$_{16}$O$_4$: C, 60.02; H, 8.00; Found: C, 60.00; H, 8.10; C, 60.14; H, 8.08.

A portion of this intermediate compound (21.10 g, 0.11 mole) was hydrogenated (1.25 g 10% Pd/C in 250 ml MeOH) at atmospheric pressure. Workup gave a saturated half-acid ester as a second intermediate as a colorless oil in quantitative yield (21.69 g).

Analysis calculated for: C$_{10}$H$_{18}$O$_4$: C, 59.43; H, 8.91, Found: C, 59.10; H. 8.71, C, 58.86; H, 8.71.

Saponification of this colorless oil (20.37 g, 0.10 mole) with 2N NaOH and recrystallization from Et$_2$O/hexane at room temperature gave 13.55 g (77% yield) of the title product as a white solid having the same properties as the compound of Example 5b.

Example 7 a.
N-[2-[2-(Hydroxyamino)-2-oxoethyl]-4-methyl-1-oxopentyl]-L-valyl-L-alaninamide (Formula I, R$^1$=—CH$_2$CH(CH$_3$)$_2$, R$^2$=—CH(CH$_3$)$_2$, R$^3$=—CH$_3$, A=H)

Following the procedure described in Example 1a, the material from Example 7b (0.14 g, 0.31 mmol) was hydrogenated and purified by flash chromatography (10:1 CHCl$_3$/MeOH) to give 83 mg (74% yield) of the title compound.

Analysis calculated for: C$_{16}$H$_{30}$N$_4$O$_5$.0.5H$_2$O: 52.30; H, 8.50; N, 15.25, Found: C, 52.00; H, 8.03; N, 15.22, C, 51.97; H, 8.11; N, 14.90.

11 b.
N-[4-Methyl-2-[2-oxo-2-(phenylmethoxyamino)ethyl]-1-oxopentyl]-L-alaninamide (Formula II, $R^1 = -CH_2CH(CH_3)_2$, $R^2 = -CH(CH_3)_2$, $R^3 = -CH_3$, A=H)

Using the procedure described in Example 1e, a portion of the material synthesized in Example 5d (1.0 g, 3.58 mmol) was coupled with ValAlaNH$_2$ (0.67 g, 3.58 mmol; ValAlaNH$_2$ was made using conventional peptide synthesis techniques). Workup followed by flash chromatography (10:1 CHCl$_3$/MeOH) gave 0.14 g (9% yield) of the title compound; R$_f$=0.29 and 0.33 (SiO$_2$ 10:1 CHCl$_3$/MeOH).

EXAMPLE 8 a.
N-[2-[2-(Hydroxyamino)-2-oxoethyl]-4-methyl-1-oxopentyl]-L-leucyl-L-phenylalanyl-L-leucinamide (Formula I with A=Formula IA, $R^1 = -CH_2CH(CH_3)_2$, $R^2 = -CH_2CH(CH_3)_2$, $R^3 = -CH_2\phi$, $R^4 = -CH_2CH(CH_3)_2$)

Employing the procedure described in Example 1a, the compound obtained in Example 8b (0.53 g, 0.81 mmol) was subjected to deprotection and flash chromatographed to give 85.2 mg (19% yield) of the title compound with a m.p. of 227°–229° C.

Analysis calculated for: C$_{29}$H$_{47}$N$_5$O$_6$·0.02H$_2$O: C, 61.61; H, 8.45; N, 12.38, Found: C, 61.77; H, 8.17; N, 12.14, C, 61.54; H, 8.02: N, 12.06.

N-[4-Methyl-2-[2-oxo-2-(phenylmethoxyamino)ethyl]-1-oxopentyl]-L-phenylalanyl-L-leucinamide (Formula II with A=Formula IA, $R^1 = -CH_2CH(CH_3)$, $R^2 = -CH_2CH(CH_3)_2$, $R^3 = -CH_2\phi$, $R^4 = -CH_2CH(CH_3)_2$)

Using the procedure described in Example 1e, a portion of the compound produced in Example 1d (1.03 g, 3.68 mmol) was coupled with LeuPheLeuNH$_2$ (1.37 g, 3.51 mmol; LeuPheLeuNH$_2$ was made using conventional peptide synthesis techniques). Workup followed by repeated flash chromatography yielded 0.53 gm (22% yield) of the title compound with a m.p. of 213°–215° C.

Analysis calculated for: C$_{36}$H$_{53}$N$_5$O$_6$·0.6H$_2$O: C, 65.23; H, 8.24; N, 10.56, Found: C, 65.34; H, 8.19; N, 11.0, C, 65.21: H, 8.45; N, 11.08.

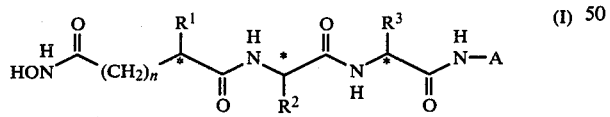
(I)

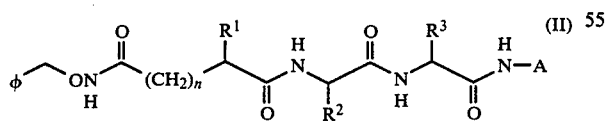
(II)

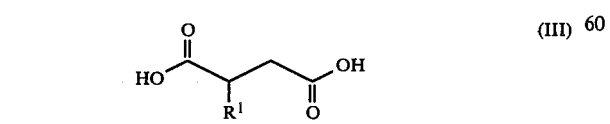
(III)

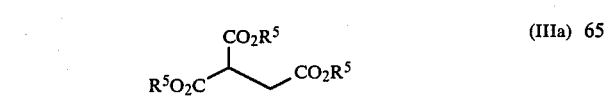
(IIIa)

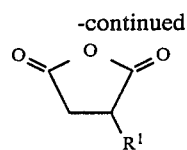
(IV)

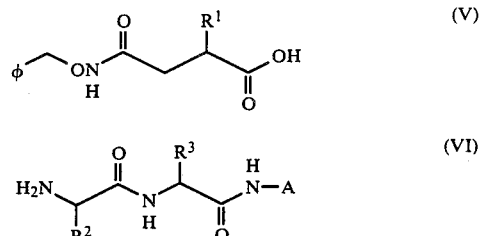
(V)

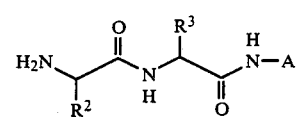
(VI)

What is claimed is:
1. A hydroxamic acid compound of formula

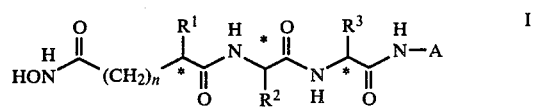
I wherein
$R^1$ is a straight or branched chain (2–7C)alkyl;
$R^2$ and $R^3$ are each an amino acid residue, wherein each said amino acid residue is independently selected from a group consisting of those derived from glycine, tyrosine, tryptophan, serine, threonine, cysteine, methionine, asparagine, glutamine, lysine, arginine, glutamic acid and aspartic acid provided that each of said amino acid residues does not have an acidic terminus, but optionally may have an acidic side chain;
n is 1 or 2; and
A is hydrogen or a group of the formula IA:

IA wherein $R^4$ is an amino acid residue, and pharmaceutically acceptable salts and maleate esters thereof.

2. A compound as claimed in claim 1 wherein
$R^1$ is selected from a group consisting of isobutyl and n-pentyl;
$R^2$ and $R^3$ are each independently selected and are each derived from a group of amino acid residues consisting of those derived from glycine, alanine, valine, leucine, isoleucine, phenylalanine, tyrosine, tryptophan, serine, threonine, cysteine, methionine, asparagine, glutamine, lysine, arginine, glutamic acid and aspartic acid, provided that each of said residues does not have an acidic terminus, but optionally may have an acidic side chain;
$R^4$ is selected from a group of particular values defined for $R^2$ and $R^3$; and
n=1.

3. A compound as claimed in claim 2 wherein
$R^1$ is isobutyl or n-pentyl;
$R^2$ is leucine or valine;
$R^3$ is alanine or phenylalanine;
n=1;
A is hydrogen.

4. A compound as claimed in claim 1 selected from a group consisting of
(a) (R.S)-N-[2-[2-hydroxyamino)-2-oxoethyl]-1-oxoheptyl]-L-leucyl-L-phenylalaninamide; (b) (R,S)-N-[2-[2-(hydroxyamino)-2-oxoethyl]-1-oxoheptyl]-L-leucyl-L-alaninamide: (c) N-[2-[2-(hydroxyamino-2-oxoethyl]-1-oxoheptyl]-L-valyl-L-alaninamide: and (d) (R,S)-N-[2-[2-(hydroxyamino)-2-oxoethyl]-4-methyl-1-oxopentyl]-L-leucyl-L-phenylalaninamide.

5. A pharmaceutical composition comprising a compound of claim 1 or a pharmaceutically acceptable salt thereof in an amount sufficient to inhibit the activity of an endopeptidase in association with a non-toxic pharmaceutically-acceptable diluent or carrier.

6. A method of antagonizing the activity of an endopeptidase comprising administering to a mammal a pharmaceutically effective amount of a compound of claim 1.

* * * * *

UNITED STATES PATENT AND TRADEMARK OFFICE
CERTIFICATE OF CORRECTION

PATENT NO. : 4,771,038

DATED : SEPTEMBER 13, 1988

INVENTOR(S) : WOLANIN ET AL

It is certified that error appears in the above-identified patent and that said Letters Patent is hereby corrected as shown below:

Column 1, line 45, "alkyl:" should read --alkyl;--.

Column 1, line 46, "residue:" should read --residue;--.

Column 2, line 14, "$R_2$" should read --$R^2$--.

Column 2, line 21, "2-oxoethyl)" should read --2-oxoethyl]--.

Column 2, line 24, "(Example 4a):" should read --(Example 4a);--.

Column 3, line 14, "page" should read --pages--.

Column 6, line 23, "(7:3)," should read --(7:3).--.

Column 6, line 24, "($MgSO_4$)." should read --($MgSO_4$),--.

Column 6, line 27, "product:" should read --product;--.

Column 7, line 9, "$R_1$" should read --$R^1$--.

Column 7, line 59, "(101°C./33.3" should read --(101°C/133.3--

Column 8, line 21, "$R_2$=-$CH_2CH(CH_3)$ hd 2, $R^3$=-$CH_3$A=H" should read --$R^2$=-$CH_2CH(CH_3)_2$, $R^3$=-$CH_3$, A=H)--.

Column 8, line 41, "Rf" should read --$R_f$--.

Column 8, line 63, "$R^1$=pentyl, $R^2$=-$CH(CH_3)_2$. $R_3$=-$CH_3$, A=H)" should read --$R^1$=n-pentyl, $R^2$=-$CH(CH_3)_2$, $R^3$=-$CH_3$, A=H)--.

Column 9, line 21, "$C_{23}H_{36}N_4O_5 \cdot 0.06H_2O$:" should read --$C_{23}H_{36}N_4O_5 \cdot 0.6H_2O$:--.

UNITED STATES PATENT AND TRADEMARK OFFICE
CERTIFICATE OF CORRECTION

PATENT NO. : 4,771,038

DATED : SEPTEMBER 13, 1988

INVENTOR(S) : WOLANIN ET AL

It is certified that error appears in the above-identified patent and that said Letters Patent is hereby corrected as shown below:

Column 10, line 9, "$R^3-CH_2\emptyset$, A=H)" should read --$R^3=-CH_2\emptyset$, A=H)--.

Column 10, line 20, "$C_{30}H_{42}N_4O_5 \cdot 0.30$:" should read --$C_{30}H_{42}N_4O_5 \cdot 0.3H_2O$:--.

Column 10, line 66, "$CH_{16}H_{30}N_4O_5 \cdot 0.5H_2O$: 52.30;" should read --$C_{16}H_{30}N_4O_5 \cdot 0.5H_2O$: C, 52.30;--.

Column 11, line 15, "($SiO_2$ 10:1 $CHCl_3$/MeOH)." should read --($SiO_2$, 10:1 $CHCl_3$/MeOH).--.

Column 11, line 29, "$C_{29}H_{47}N_5O_6 \cdot 0.02H_2O$:" should read --$C_{29}H_{47}N_5O_6 \cdot 0.2H_2O$--.

Column 11, line 34, "$R^1=-CH_2CH(CH_3)$ ," should read --$R^1=-CH_2CH(CH_3)_2$,--.

Signed and Sealed this

Eleventh Day of July, 1989

Attest:

DONALD J. QUIGG

Attesting Officer

Commissioner of Patents and Trademarks